United States Patent
Teisen et al.

(10) Patent No.: US 9,572,676 B2
(45) Date of Patent: Feb. 21, 2017

(54) ADJUSTABLE MULTI-VOLUME BALLOON FOR SPINAL INTERVENTIONS

(71) Applicant: DePuy Synthes Products, Inc., Raynham, MA (US)

(72) Inventors: Jacques Teisen, Zurich (CH); Joern Richter, Kandern (DE); Richard Assaker, Kain (BE)

(73) Assignee: DePuy Synthes Products, Inc., Raynham, MA (US)

( * ) Notice: Subject to any disclaimer, the term of this patent is extended or adjusted under 35 U.S.C. 154(b) by 327 days.

(21) Appl. No.: 13/827,060

(22) Filed: Mar. 14, 2013

(65) Prior Publication Data

US 2014/0277466 A1  Sep. 18, 2014

(51) Int. Cl.
| | |
|---|---|
| *A61F 2/44* | (2006.01) |
| *A61B 17/88* | (2006.01) |
| *A61F 2/30* | (2006.01) |

(52) U.S. Cl.
CPC .......... *A61F 2/441* (2013.01); *A61B 17/8852* (2013.01); *A61B 17/8855* (2013.01); *A61F 2/442* (2013.01); *A61F 2/4455* (2013.01); *A61F 2002/30062* (2013.01); *A61F 2002/30586* (2013.01); *A61F 2002/30588* (2013.01)

(58) Field of Classification Search
CPC ............ A61F 2/441; A61F 2002/4415; A61B 17/885; A61B 17/8852; A61B 17/8855
See application file for complete search history.

(56) References Cited

U.S. PATENT DOCUMENTS

| | | | | |
|---|---|---|---|---|
| 3,211,152 | A | * 10/1965 | Stern | .......................... 128/207.15 |
| 4,077,394 | A | * 3/1978 | McCurdy | ......................... 600/18 |
| 4,512,766 | A | * 4/1985 | Vailancourt | ....... A61M 39/0613 |
| | | | | 251/149.1 |
| 4,856,510 | A | * 8/1989 | Kowalewski | ............ 128/207.15 |
| 5,181,921 | A | 1/1993 | Makita et al. | |
| 5,306,310 | A | 4/1994 | Siebels | |
| 5,423,850 | A | 6/1995 | Berger | |
| 5,772,661 | A | 6/1998 | Michelson | |
| 5,827,289 | A | * 10/1998 | Reiley et al. | ............... 606/86 R |

(Continued)

FOREIGN PATENT DOCUMENTS

| | | |
|---|---|---|
| DE | 10 2005 034 529 A1 | 1/2007 |
| EP | 1 913 903 A2 | 4/2008 |

(Continued)

OTHER PUBLICATIONS

Written Opinion for Application No. PCT/US2014/021266, mailed Sep. 2, 2014 (10 Pages).

(Continued)

*Primary Examiner* — Zade Coley
(74) *Attorney, Agent, or Firm* — Nutter McClennen & Fish LLP

(57) ABSTRACT

An inflatable balloon for diagnostics and treatment of diseased discs or fractured bones. The balloon is a multi-volume balloon comprised of a plurality of adjustable and expandable single volumes. Further disclosed are methods of forming, expanding, and implanting the multi-volume balloon for proper placement and stabilization of the diseased discs or fractured bones. Still further disclosed are kits for aligning and stabilizing a bone, disc, or spinal motion segment.

18 Claims, 4 Drawing Sheets

(56) References Cited

U.S. PATENT DOCUMENTS

| | | | |
|---|---|---|---|
| 6,066,154 A * | 5/2000 | Reiley et al. | 606/192 |
| 6,228,022 B1 | 5/2001 | Friesem et al. | |
| 6,468,200 B1 * | 10/2002 | Fischi | 600/18 |
| 6,582,451 B1 | 6/2003 | Marucci et al. | |
| 6,607,544 B1 * | 8/2003 | Boucher et al. | 606/192 |
| 6,632,235 B2 * | 10/2003 | Weikel et al. | 606/192 |
| 6,679,886 B2 | 1/2004 | Weikel et al. | |
| 6,712,853 B2 | 3/2004 | Kuslich | |
| 6,811,558 B2 | 11/2004 | Davison et al. | |
| 7,056,345 B2 | 6/2006 | Kuslich | |
| 7,074,226 B2 | 7/2006 | Roehm, III et al. | |
| 7,108,705 B2 | 9/2006 | Davison et al. | |
| 7,267,687 B2 | 9/2007 | McGuckin, Jr. | |
| 7,300,456 B2 | 11/2007 | Andreas et al. | |
| 7,503,920 B2 | 3/2009 | Siegal | |
| 7,618,367 B2 | 11/2009 | Martin et al. | |
| 7,618,431 B2 | 11/2009 | Roehm, III et al. | |
| 7,643,884 B2 | 1/2010 | Pond, Jr. et al. | |
| 7,666,205 B2 * | 2/2010 | Weikel et al. | 606/192 |
| 7,666,226 B2 | 2/2010 | Schaller | |
| 7,666,227 B2 | 2/2010 | Schaller | |
| 7,670,374 B2 | 3/2010 | Schaller | |
| 7,670,375 B2 | 3/2010 | Schaller | |
| 7,740,659 B2 | 6/2010 | Zarda et al. | |
| 7,785,368 B2 | 8/2010 | Schaller | |
| 7,918,874 B2 | 4/2011 | Siegal | |
| 7,947,078 B2 | 5/2011 | Siegal | |
| 7,955,391 B2 | 6/2011 | Schaller | |
| 7,955,931 B2 | 6/2011 | Appenzeller et al. | |
| 7,963,993 B2 | 6/2011 | Schaller | |
| 7,967,864 B2 | 6/2011 | Schaller | |
| 7,967,865 B2 | 6/2011 | Schaller | |
| 8,007,535 B2 | 8/2011 | Hudgins et al. | |
| 8,012,197 B2 | 9/2011 | Bashiri et al. | |
| 8,057,544 B2 | 11/2011 | Schaller | |
| 8,236,057 B2 * | 8/2012 | Wirtel et al. | 623/17.12 |
| 8,460,383 B2 * | 6/2013 | Wirtel et al. | 623/17.12 |
| 8,518,118 B2 | 8/2013 | Sack et al. | |
| 9,358,120 B2 | 6/2016 | Richter et al. | |
| 2002/0013601 A1 * | 1/2002 | Nobles et al. | 606/193 |
| 2003/0018390 A1 | 1/2003 | Husson | |
| 2004/0230309 A1 | 11/2004 | DiMauro et al. | |
| 2005/0070900 A1 * | 3/2005 | Serhan | A61B 17/3468 623/17.12 |
| 2005/0278027 A1 | 12/2005 | Hyde | |
| 2007/0055265 A1 | 3/2007 | Schaller | |
| 2007/0123986 A1 | 5/2007 | Schaller | |
| 2007/0162136 A1 | 7/2007 | O'Neil et al. | |
| 2007/0288095 A1 * | 12/2007 | Wirtel et al. | 623/17.16 |
| 2008/0133012 A1 | 6/2008 | McGuckin | |
| 2008/0154272 A1 | 6/2008 | Schaller et al. | |
| 2008/0234687 A1 | 9/2008 | Schaller et al. | |
| 2008/0234827 A1 | 9/2008 | Schaller et al. | |
| 2009/0088788 A1 * | 4/2009 | Mouw | 606/192 |
| 2009/0118833 A1 | 5/2009 | Hudgins et al. | |
| 2009/0182386 A1 | 7/2009 | Schaller | |
| 2009/0222096 A1 | 9/2009 | Trieu | |
| 2009/0234454 A1 | 9/2009 | Siegal | |
| 2009/0234457 A1 | 9/2009 | Lotz et al. | |
| 2009/0248159 A1 | 10/2009 | Aflatoon | |
| 2009/0275913 A1 | 11/2009 | Trieu | |
| 2010/0198263 A1 | 8/2010 | Siegal et al. | |
| 2010/0234954 A1 | 9/2010 | Justis et al. | |
| 2010/0241177 A1 | 9/2010 | Schaller et al. | |
| 2010/0249505 A1 * | 9/2010 | Shoham et al. | 600/115 |
| 2010/0262147 A1 | 10/2010 | Siegal et al. | |
| 2010/0262242 A1 * | 10/2010 | Chavatte et al. | 623/17.12 |
| 2011/0004307 A1 | 1/2011 | Ahn et al. | |
| 2011/0046737 A1 | 2/2011 | Teisen | |
| 2011/0066192 A1 | 3/2011 | Frasier et al. | |
| 2011/0092859 A1 | 4/2011 | Neubardt | |
| 2011/0118789 A1 | 5/2011 | Siegal | |
| 2011/0137332 A1 | 6/2011 | Sepetka et al. | |
| 2011/0152683 A1 * | 6/2011 | Gerrans et al. | 600/435 |
| 2011/0153019 A1 | 6/2011 | Siegal | |
| 2011/0172710 A1 * | 7/2011 | Thommen et al. | A61B 17/7065 606/249 |
| 2011/0178523 A1 | 7/2011 | Siegal et al. | |
| 2011/0184515 A1 | 7/2011 | Siegal | |
| 2011/0202133 A1 | 8/2011 | Siegal | |
| 2011/0218494 A1 * | 9/2011 | Gerrans et al. | 604/101.05 |
| 2011/0230967 A1 | 9/2011 | O'Halloran et al. | |
| 2011/0245926 A1 | 10/2011 | Kitchen | |
| 2011/0264146 A1 | 10/2011 | Siegal | |
| 2011/0307063 A1 | 12/2011 | Schaller | |
| 2011/0307064 A1 | 12/2011 | Schaller | |
| 2012/0116399 A1 * | 5/2012 | Appenzeller | A61B 17/7097 606/63 |
| 2012/0191125 A1 * | 7/2012 | Babkes | A61F 5/0036 606/192 |
| 2012/0259215 A1 * | 10/2012 | Gerrans et al. | 600/435 |
| 2012/0259216 A1 * | 10/2012 | Gerrans et al. | 600/435 |
| 2014/0107789 A1 | 4/2014 | Schaller et al. | |
| 2014/0277464 A1 | 9/2014 | Richter et al. | |
| 2014/0277465 A1 | 9/2014 | Teisen et al. | |
| 2016/0250032 A1 | 9/2016 | Richter et al. | |

FOREIGN PATENT DOCUMENTS

| | | |
|---|---|---|
| WO | 03/059213 A2 | 7/2003 |
| WO | 2007/022194 A2 | 2/2007 |
| WO | 2007/076049 A2 | 7/2007 |
| WO | 2008/063435 A1 | 5/2008 |
| WO | 2008/103781 A2 | 8/2008 |
| WO | 2008/103832 A2 | 8/2008 |
| WO | 2009/006432 A2 | 1/2009 |
| WO | 2013/023898 A1 | 2/2013 |

OTHER PUBLICATIONS

International Search Report for Application No. PCT/US2014/021236, mailed Jun. 13, 2014 (7 Pages).

International Search Report for Application No. PCT/US2014/021248, mailed Jun. 27, 2014 (7 Pages).

International Search Report for Application No. PCT/US2014/021266, mailed Sep. 2, 2014 (9 Pages).

* cited by examiner

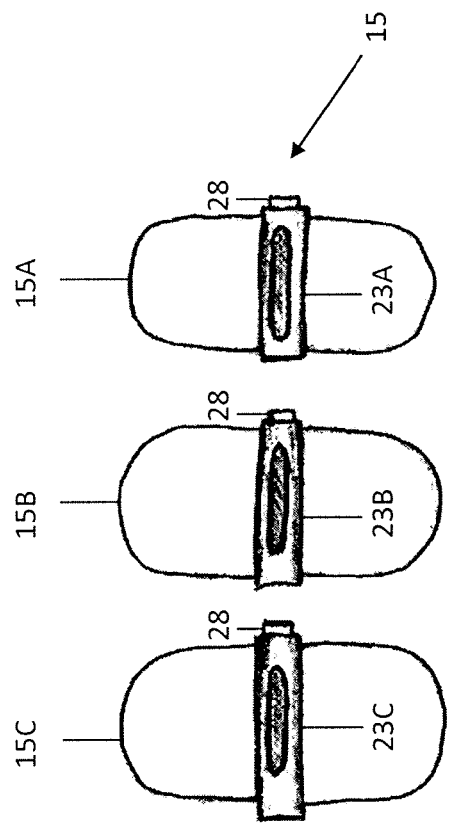
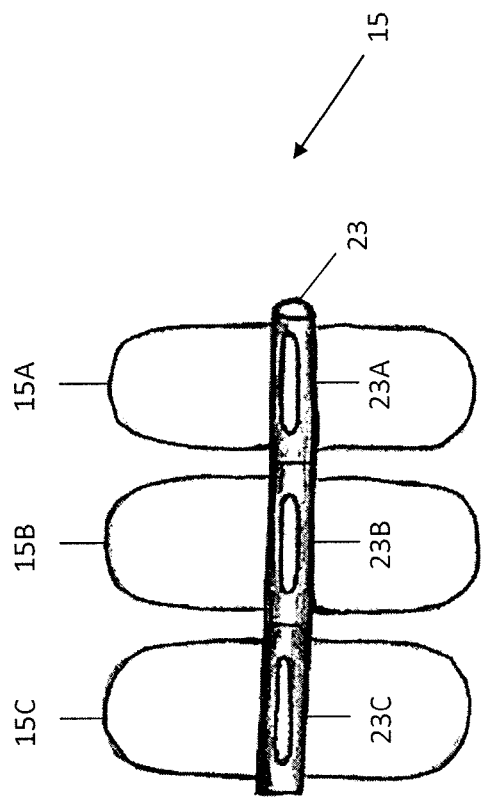
FIG. 2A
FIG. 2B

ADJUSTABLE MULTI-VOLUME BALLOON FOR SPINAL INTERVENTIONS

TECHNICAL FIELD

The technical field relates generally to inflatable and implantable balloons for treating degenerative disc disease, bones lesions, spinal deformities and spinal motion segment instabilities, and, more particularly, to adjustable multi-volume balloons and methods of using the adjustable multi-volume balloons within the intervertebral disc space, vertebral bodies, interspinous space, and/or any other spinal elements, to aim at restoring the original anatomy of the spine.

BACKGROUND

Expandable medical implants, for example balloons, are commonly used for dilating and unblocking clogged or narrowed arteries (angioplasty). More recently, balloons have been used in surgical contexts other than angioplasty because the implants can be introduced into a surgical site with a reduced profile to minimize disruption of the surrounding tissues, nerves, and blood vessels.

In the context of vertebral reconstruction, balloons could be particularly useful. Vertebral reconstruction procedures, including percutaneous procedures such as kyphoplasty or vertebral body stenting, are used to correct a fractured vertebrae, a spinal deformity, or spinal instability, while intervertebral procedures, such as open surgery spinal fusion procedures, are used to correct the loss of disc height due to degenerative or herniated discs. Balloons using percutaneous procedures are not yet known to be commonly used in spinal fusion and intervertebral disc replacement procedures. Classic spinal fusion procedures are often effective to restore proper vertebral spacing and therefore relieve pressure on nerves and consequent pain, despite the huge open wounds and subsequent surgical trauma involved.

A problem with currently used fusion procedures occurs when two vertebral bodies are fused together because eventually the lack of an intervertebral disc between the two fused vertebral bodies overloads the adjacent intervertebral discs accelerating the degeneration of these adjacent discs. One treatment option is an intervertebral disc replacement, such as a prosthetic disc. This procedure is also used in patients with degenerative or herniated discs. A problem associated with a prosthetic disc is the vertebral bodies may need varying support in different locations. Pressure distribution on the damaged intervertebral disc may no longer be uniform, due to the years of damage to the spine that typically occurs before surgery is considered. Therefore, a prosthetic disc may not provide the necessary support to the vertebral bodies.

Another issue related to use of implants is that diseases, such as degenerative disc disease (DDD), are dynamic diseases: the intervertebral disc degenerates progressively and presents a variety of symptoms, and therefore treatment options. Disc degeneration is a normal part of the aging process and may not be an issue for a normal person. For an individual with DDD, however, a degenerated disc can cause severe chronic pain and lead to chronic debilitating conditions if left untreated. In some patients, DDD can be treated without surgery, but if non-surgical treatment options are unsuccessful, surgery is typically recommended. The surgical option selected for a patient depends on the stage of disc degeneration, i.e., early-, mid-, or late-stages of degeneration. Some examples of surgical procedures include: discec-tomy, corpectomy, fusion, dynamic stabilization, intervertebral disc arthroplasty (also called Artificial Disc Replacement (ADR)), and spinal decompression. Once traditional surgical procedures, such as fusion, are used to treat DDD, there is an increased rate of re-operation for patients to treat additional problems associated with DDD. One solution to this problem is to provide a method of treatment for DDD that allows a patient to retain mobility and preserve the range of motion to minimize the need for re-operation.

As one skilled in the related art would readily appreciate, there is a continuing need for new and innovative medical implants and insertion devices directed toward the treatment of diseased and damaged bones. More specifically, there exists a need for medical implants that provide maximum support and ease of positioning within a cavity of bone. There is a similar need for treatment options for the clinical consequences of DDD, vertebral body bone defects, and spinal motion segment instability that can be customized for the patient as disc degeneration progresses.

SUMMARY

To meet these and other needs, and in view of its purposes, the disclosure provides a multi-volume balloon for treating the clinical consequences of degenerative disc disease, vertebral body bone defects, and spinal motion segment instability. The multi-volume balloon has a plurality of single volumes. The single volumes are each connected, directly or indirectly, to one another. Each single volume is individually adjustable and expandable such that (a) each single volume can contain a variable volume of contents, and (b) each of the plurality of single volumes can contain the same, or a different, volume of contents relative to another single volume balloon.

The present application also provides several methods for treating the clinical consequences of degenerative disc disease, vertebral body bone defects, and spinal motion segment instability. In one embodiment, the method includes the step of inserting an unexpanded multi-volume balloon having a proximal end and a distal end, wherein the multi-volume balloon contains a perforated guide tube, into a cavity of a vertebral column, wherein the cavity is an intervertebral disc space, an interspinous space, or a vertebral body. An inner tube is inserted into the perforated guide tube at an insertion site, wherein the inner tube is attached to a delivery tube. The delivery tube is secured to the perforated guide tube to create a seal at the insertion site. A first volume of the multi-volume balloon most distal from the insertion site is expanded by providing contents to the first volume of the multi-volume balloon through the inner tube. The volume of contents delivered is adjustable and variable, and the expansion provides a correction to the vertebral column. The inner tube is retracted to a second more proximal volume of the multi-volume balloon. The second more proximal volume of the multi-volume balloon is expanded by providing contents to the second more proximal volume through the inner tube wherein the expansion provides a further correction to the vertebral column. The inner tube is retracted from the perforated guide tube. The insertion site is sealed and the total correction made to the bone by the expansion of the multi-volume balloon is determined.

In another embodiment, the method includes the step of inserting a first single-volume balloon into an insertion site of a cavity of a vertebral column, wherein the cavity is an intervertebral disc space or a vertebral body, wherein the first single-volume balloon includes a first ring on the proximal end of the single-volume balloon. A delivery tube is connected to the first ring. The first single-volume balloon is expanded with contents delivered through the delivery tube. The expanded first single-volume balloon is sealed with the first ring. A second single-volume balloon is inserted in the insertion site of the cavity of the vertebral column, wherein the first ring around the first single-volume balloon guides the insertion of the second single-volume balloon. The expanded first single-volume balloon is punctured through the first ring. A distal portion of the second single-volume balloon is inserted into the first single-volume balloon via the puncture site through the first ring. The delivery tube is connected to a second ring on the proximal end of the second single-volume balloon. The second single-volume balloon is expanded with contents delivered through the delivery tube wherein the distal portion of the expanded second single-volume balloon is expanded within the first single-volume balloon, the first ring around the first single-volume balloon creates a seal between the expanded second single-volume balloon and the expanded first single-volume balloon, and the connected first and second single-volume balloons form a multi-volume balloon. The expanded second single-volume balloon is sealed with the second ring, and a correction made to the vertebral column from the inflation of the first and second single-volume balloons is determined.

The method of still another embodiment involves aligning and stabilizing a vertebral column. The method includes the step of inserting a multi-volume balloon into a cavity of a vertebral column, wherein the cavity is an intervertebral disc space or a vertebral body. A first volume of the multi-volume balloon is expanded by inserting saline, wherein the expansion of the first volume restores height to the vertebral column. A second volume of the multi-volume balloon is expanded by inserting a polymer, wherein the polymer hardens after insertion to maintain the height restoration created by the expansion of the first volume.

The present application also provides a kit for aligning and stabilizing bone. In one embodiment, the kit includes a multi-volume balloon having a plurality of adjustable single-volume balloons each connected, directly or indirectly, to one another. Each single-volume balloon is individually adjustable and expandable such that (a) each single-volume balloon can contain a variable volume of contents, and (b) each of the plurality of single-volume balloons can contain the same, or a different, volume of contents relative to another single-volume balloon. The kit further includes a perforated guide tube contained within the multi-volume balloon. The kit still further includes an inner tube adapted to be inserted into the perforated guide tube wherein the inner tube is capable of delivering contents to the plurality of single-volume balloons. A delivery tube of the kit is adapted to be connected both to the inner tube and to the perforated guide tube.

It is to be understood that both the foregoing general description and the following detailed description are exemplary, but are not restrictive, of the embodiments of the present application.

BRIEF DESCRIPTION OF THE DRAWING

The foregoing summary and the following detailed description of illustrative embodiments are best understood when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 2A and FIG. 2B are perspective views of a single-volume balloon mounted into a multi-volume balloon according to another embodiment;

DETAILED DESCRIPTION OF THE ILLUSTRATIVE EMBODIMENTS

Figure 1:
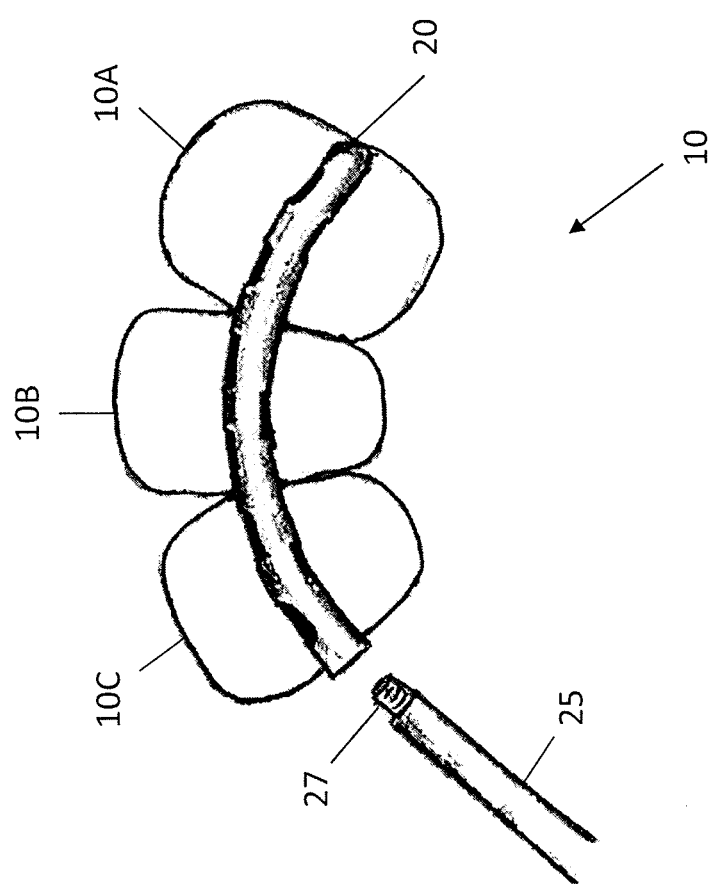
FIG. 1 is a perspective view of a multi-volume balloon according to one embodiment.

Certain terminology is used in the following description for convenience only and is not limiting. The words "right," "left," "lower," and "upper" designate directions in the figures to which reference is made. The words "inwardly" and "outwardly" refer to directions toward and away from, respectively, the geometric center of the multi-volume balloon. The words "anterior," "posterior," "superior," "inferior," and related words or phrases designate preferred positions and orientations in the human body to which reference is made and are not meant to be limiting. The terminology includes the above-listed words, derivatives of those words, and words of similar import.

The clinical consequences of degenerative disc disease, vertebral body bone defects, and spinal motion segment instability can be treated by either restoring height to the intervertebral disc or by stabilizing the vertebral body. Treatment addresses a lesion zone "cavity" within the vertebral column. A cavity can include either the space previously occupied by the intervertebral disc, a space within a vertebral body, an interspinous space, or a space created by the balloon(s) itself by dilatation. The multi-volume balloons reclaim both the disc space (i.e., they act as disc spacers) and the disc itself, and/or provide posterior stabilization of the spine. The balloons maintain the dampening function of the disc spacers and protect adjacent levels when a soft filler is used that allows for elastic deformation of the construct. In some embodiments, the balloons can assist in the fusion of any two bodies, preferably vertebral bodies.

A benefit of the multi-volume balloon approach to stabilization and fusion of vertebral bodies is that a surgeon, or caregiver, can adjust and specify the individual volumes of the multi-volume balloon to provide maximum stabilization and spinal realignment within a cavity of the vertebral column. For example, if a degenerative disc results in a vertebral body sloping inferiorly on the left side of the patient's body, a single volume of the multi-volume balloon supporting that area need not be as inflated as a single volume of the multi-volume balloon on the right side of the patient's body. In traditional single volume balloons, this variance in volumes could not be accomplished with such a balloon by itself. The embodiments of the multi-volume balloon provide for individualized, variable, and adjustable volumes of support from the multi-volume balloon. Further, a single-volume balloon typically provides support in the center of the vertebral body, the weakest part of the bone. The multi-volume balloon provides support on an individualized basis that is form-fitting to the anatomy of the patient and can target the peripheral edges of the vertebral bone to support the bone where the bone is most durable; this individualized support provides for improved load distribution and force application with multiple compartments, volumes, and/or balloons.

The multi-volume balloons may be used to treat any bone with an interior cavity or space sufficiently large to receive the balloon. Non-limiting examples of bones that are suitable candidates for anatomical restoration using embodiments of the device, method, and kit include vertebral bodies, the medullary canals of long bones, the calcaneus, and the tibial plateau. The multi-volume balloon can be designed and adapted to accommodate particular bone anatomies and different cavity shapes, which may be made in these and other suitably large bones.

The material of the balloon is selected based on the intended purpose of the balloon. For example, if one of the volumes of the balloon is used to lift a vertebral body by occupying the intervertebral disc space, the material is thick-walled to accommodate the stress of lifting a vertebral body; if one of the volumes of the balloon is used to provide a cushioning/dampening effect, the material is more elastic in order to permit variances in volumes or shaping of the balloon. In some embodiments, during a cushioning or dampening procedure, the volume of the balloon remains constant; the cushioning or dampening effect is achieved by elastic deformation of the contents and therefore the balloon. The balloon may also be made of a rigid or non-elastic material, such as, for example, foil or foil coated with a protective material. The balloon may be thick-walled to contain liquids for an extended period of time, i.e., beyond the lifting of a vertebral body. The multi-volume balloon may be designed and configured to be deployed and remain in the bone cavity for an extended period of time. Balloons can be made of any suitable material to provide for inflation and/or stabilization, such as, for example, foil, mesh, silicone rubber, elastomeric rubber, polyether ether ketone (or PEEK), polyether ketone ketone (or PEKK), polyethelyene (or PE), polyurethane (or PU), polycarbonate urethane (or PCU), polyethylene terephthalate (or PET), thermoplastic polyurethane (or TPU), etc. Any one of a diverse set of polymers is preferred. Balloon materials for temporary use may include polyamides (or PA) and co-polymers thereof, e.g., polyether-block-amide (or PEBA, Pebax), allowing for suitable balloon material compliance tuning. A balloon made with softer, more elastic substances is better for correcting load distribution while a harder balloon is better for realignment and space maintenance. In another embodiment, the balloon may be biologically resorbable. Biologically resorbable balloon materials may include polylactides, magnesium alloy components, etc.

Once filled, the balloon is allowed to remain within the intervertebral disc space or bone for a prescribed period of time or perhaps indefinitely. The duration of time that the balloon remains within the bone may depend upon specific conditions in the treated bone and the particular objective sought by the treatment. When the balloon is implanted for a short period of time (e.g., just during surgery or for several weeks to months after surgery), it functions as an intraoperative and/or post-operative instrument or diagnostic device in creating space, or lifting the vertebral body, and/or providing stabilization in order to evaluate the effect on the patient's constitution during or after the surgery. Alternatively, the balloon functions as an implant when it remains in the patient for longer periods of time. The balloon may remain within the cavity for prescribed periods of time that include, for example, an hour, a day, several days, weeks, months, or years, or even may remain within the bone permanently.

The balloon content material can be any one or a combination of a number of: liquids, such as, for example, water, saline solutions, radiopaque contrast medium solutions; elastic-type contents, such as, for example, elastomers (especially silicone-based), hydrogels, silicone; rigid contents, such as, for example, polymethyl methacrylate (PMMA), hydroxylapatide-based materials, calciumphosphate-based materials, and other bone cements; particles, such as, for example, bone, polymers, bone chips in a liquid; and bioabsorbable materials. Bone cements may provide a rigid construct or be elastic; both the rigidity and elasticity may be reached in-situ via a chemical reaction, such as polymerization or crystallization reactions. Aqueous liquids (such as saline, contrast media, mixes thereof, etc.) as well as elastomers provide a dampening cushion. The dampening cushion provided by the device is designed to restore any weakened/damaged structures that are adjacent to the balloon, as well as to protect any intact/healthy structures that are adjacent to the balloon. A problem with the current fusion procedure, which fuses two vertebral bodies together, is eventually the fused vertebral bodies create the same issue in the adjacent intervertebral discs because nearby intervertebral discs compensate for the lack of an intervertebral disc of the fused bodies and therefore are overloaded. In contrast, embodiments of the balloon provide a dampening effect in the treated level by providing a cushion effect and therefore protecting the adjacent level from overloading.

The content material can also be a two-component mixture, for example, bone chips with a hardening agent. Fluids such as liquids are also possible, but require sealing, using, for example, valves, crimped ends, glued ends, rivets at the ends, or any other leakage-avoiding sealing of any open ends. A thick-walled balloon is recommended if the balloon will be filled with liquid and implanted for an extended period of time. A seal according to an embodiment creates a leak-proof closure to prevent the contents of the balloon from leaking out and creates continuity between the series of single-volume balloons to form a multi-volume balloon. One embodiment involves inserting a liquid into the balloon, where the expanded balloon is used as an instrument to lift the vertebral body to a desired height. A second balloon or lumen may then be inserted and inflated to permanently restore height to the vertebral body. The liquid is then removed from the balloon and the balloon is removed from the patient. Once height is restored, bone cement, a cage, a subsequent balloon filled with contents selected based on the stage of disc degeneration, or any other device can be inserted to occupy the space created by the balloon or created in the surrounding of the balloon.

The content material can be heated above body temperature (about 98.6° F.) so that it hardens faster (approximately 140° F.-160° F.); applied heating accelerates hardening of the content material. The content material is heated, rather than the entire balloon or even the walls of the balloon. An example of a preferred content material that can be selectively heated includes polymethyl methacrylate (or PMMA). The heat can be selectively applied to the content material of discrete volumes of the balloon. A heat probe can be affixed to the device to accelerate the chemical reaction in order to harden the contents of the balloon. The heat can be applied after insertion of the multi-volume balloon into the patient. A benefit is that, once the balloon is filled, the balloon can remain within the body of the patient. The content material hardens, either by body temperature alone or by the application of additional heat to harden the contents, within the balloon and there is no concern for leakage of the material from the balloon because it is a hardened material. Especially if the balloon is to remain within the body for an extended period of time, the contents of the balloon must be biocompatible because of potential mechanical degeneration or tearing of the balloon itself. Alternatively, the entire balloon is heated because the heat may not alter the balloon wall while the contents are hardened.

The content material can be provided under precise pressure control to achieve two advantages: (1) to have total control over the procedure of recreating a volume/lifting vertebral bodies; and (2) to measure and/or correlate the applied pressure to the applied force as a safety feature in order not to exceed a given maximal force, i.e., using a smart instrument. In a preferred embodiment, the multi-volume balloon is inflated directly against the bone to be restored. This causes the deployed balloon to press the damaged bone into a configuration that reduces fractures and restores the anatomy of the damaged bone and provides for the balloon to form fit to the anatomy of the cavity.

The balloons are particularly useful for treatment of DDD (degenerative disc disease), vertebral body bone defects, and spinal motion segment instability. Methods according to an embodiment provide for customizing the location and the contents of the balloons based upon the stage, or progression, of disc degeneration in a patient. In early-stages of degeneration, the methods provide for dynamic stabilization of the spine. Dynamic stabilization of the spine is accomplished by a variety of methods including: (1) providing anterior support to the spine by inserting a balloon into the intervertebral disc space where the annulus fibrosus of the intervertebral disc remains intact; (2) providing anterior support to the spine by inserting a balloon into the disc space where the nucleus pulposus and annulus fibrosus have been removed; (3) providing posterior support to the spine by inserting a balloon into the interspinous space and leaving the intervertebral disc intact; or (4) providing 360° dynamic stabilization by (a) removing the nucleus pulposus and annulus fibrosus, (b) providing anterior support by inserting a balloon into the intervertebral disc space, and (c) providing posterior support by inserting a balloon into the interspinous space. The methods further provide for filling the balloons with non-rigid contents, such as, for example a saline solution, hydrogel, elastomer (or elastomer cement), or silicone-type material; the non-rigid contents allow for elastic movement and preserve motion for the patient. In early stages of degeneration, the method provides for an adjacent level of protection, stabilization of disc height, supporting transition levels, and decelerating degeneration. The combination of the location, type of balloon, and contents of the balloon provide for dampening effects and protect the adjacent levels of the vertebral column. In some embodiments, devices, methods, and kits described in this application can be used for multiple levels of treatment, i.e., to treat more than one level of the spine of a patient.

In mid-level stages of disc degeneration, the method provides for balloon fusion techniques. After removal of the intervertebral disc (discectomy), a balloon can be inserted in the anterior position of the vertebral endplate to allow for bony fusion to take place. In addition to the anterior balloon, in some embodiments, another balloon is inserted into the interspinous space to provide additional posterior support and result in 360° bony fusion stabilization. Alternatively, the anterior balloon can be used in combination with a facet wedge system that blocks the facet joints in order to stabilize the motion segment and achieve a bony fusion. The small dimensions in diameter of an anterior balloon system (inner working channel diameter is 3 mm to 12 mm) render it possible to achieve additional stabilization by retaining intact the facet joints of the vertebral body (other than the current, e.g., Transforaminal Lumbar Interbody Fusion (TLIF) or Posterior Lumbar Interbody Fusion (PLIF) approaches). A surgeon can therefore use a facet wedge system that blocks the facet joints in order to stabilize the motion segment and achieve a bony fusion (360° stabilization). In mid-level stages of disc degeneration, preferred content material includes bone cements; rigid compound materials, such as, for example, hydroxylapatide-based materials and calciumphosphate-based materials; and particle materials. In mid-level stages of degeneration, the method provides for a rigid construct to allow for bony fusion to occur, especially at the peripheral edges of the vertebral bodies, restoration of sagittal balance and disc height, and stabilization of the vertebral bodies to protect existing structures.

In late stages of disc degeneration, embodiments provide for discoplasty or a balloon that completely covers the endplate of the vertebral body and due to a permeability towards the vertebral body endplates allows for a penetration of filler through the endplates into the vertebral bodies, i.e., primary stabilization and augmentation. The preferred content materials include bone cements and rigid compound materials, such as, for example, hydroxylapatide-based materials and calciumphosphate-based materials. In some embodiments, in order for the balloon to provide stability of the construct and achieve further stabilization, the balloon has openings to allow for penetration of the rigid filling into the vertebral bodies. Therefore, this type of semipermeable balloon could also be considered to be a safety device that prevents the content material from uncontrolled leakage out of the disc space. The openings in the balloon can be created by holes or pores, or the balloon can be made from a mesh-type material. In late-level stages of degeneration, the method provides for disc immobilization in osteoporotic segments.

Determining the necessary location of the balloons and contents may be difficult because of the progressive characteristics of disc degeneration from early-, to mid-, to late-stages of disc degeneration. One purpose of the method is to match the location of the balloons and contents of the balloon to the progression of the disease or disc degeneration. The content material in the balloon can be removed and replaced with a different filler as the disease progresses.

In some embodiments of the invention, using water, or saline solution (with or without a contrast medium, e.g., iodine-based or gadolinium-based), or a non-rigid fluid or solution, for the contents of the balloon is for diagnostic purposes or for temporary pain relief. Specifically, if a surgeon is unsure whether the placement of the balloon, the amount of contents, or the number of volumes in the balloon would alleviate any pain, discomfort, or other symptoms a patient may have, the surgeon inserts a balloon, fills the balloon with saline, and determines if a correction has been made. The determination of the correction can be made in the operating room or at any time post-operatively, such as, for example, days, weeks, or months after the operation. If the patient is satisfied with the result, the saline solution can then be removed from the balloon and the balloon filled with different contents, depending upon the progression of the disc degeneration.

In addition, the outer surface of the balloon may be treated with a coating or texture to help the balloon become more integral with the surrounding bone matter or to facilitate acceptance of the balloon by the patient. The selection of balloon materials, coatings, and textures also may help prevent rejection of the balloon by the body. The inner surface of the balloon likewise may be textured or coated to improve the performance of the balloon. For instance, the inner surface of the balloon may be textured to increase adhesion between the balloon wall and the material inside.

The multi-volume balloon is inserted into a bone cavity or disc space that has been prepared to allow the balloon to be placed in the disc space or near the damaged bone. In some embodiments, the cancellous tissue and bone marrow inside the bone and in the area to be treated are cleared from the region in advance of deploying the balloon. Clearing the treated region may be accomplished by either shifting or relocating the cancellous bone and marrow to untreated regions inside the bone, or by removing the materials from the bone by using a reamer or some other device. Alternatively, a discectomy can be performed to remove the intervertebral disc. These methods are particularly useful in embodiments where devices to promote fusion are inserted after the balloon.

In addition, the bone cavity or disc space may be irrigated and/or aspirated to permit balloon implantation and to create an environment suitable for bone growth. Preferably, the aspiration is sufficient to remove bone marrow within the region to be restored. In particular, a region as big as the fully deployed multi-volume balloon should be aspirated in this manner. More preferably, a region exceeding the extent of the fully deployed balloon by about 2 mm to 4 mm is aspirated in this manner. Clearing the cavity of substantially all bone marrow near or within the treated region may prove especially useful for restoring the bone and incorporating the balloon as a prosthetic device to remain in the cavity. U.S. Pat. No. 6,679,886 issued to Weikel et al. entitled "Tools and methods for creating cavities in bone" (the contents of which are incorporated by reference) describes a method for creating cavities in bone. In another embodiment, the intervertebral disc or disc space does not need to be cleared out before putting the balloon in the disc space. In this embodiment, a guide wire, preferably a pre-bent guide wire, guides the balloon to the disc space and expands the balloon. The guide-wire can be made from a shape-memory alloy such as nitinol and have a pre-determined bend created by shape-setting processing.

In some embodiments, a cavity may be pre-created by inserting a balloon, such as a spherical balloon, into the cavity of the patient. In this embodiment, the balloon is inserted into the patient, the balloon is expanded, thus creating the cavity, and removed. A balloon according to this embodiment is then inserted into the pre-created cavity and can be unfurled, expanded, and/or inserted into the cavity of the patient. The balloon would meet much less resistance in the pre-created cavity than it would in a cavity that is filled with cartilage, bone, etc.

Access can be paved for the balloons using a posterior minimally invasive surgery (MIS) via a 3 mm to 12 mm diameter cannula and the facet joints of the vertebrae remain intact, or even using a posterior percutaneous approach of only 1 mm to 4 mm. A device inserted via a posterior approach is limited in size by the interval between the nerve roots and the existing bony structures. Therefore, the multi-volume balloon of certain embodiments is expanded from within the intervertebral space or cavity to reduce potential trauma to the nerve roots and yet still allow restoration of disc space height. Alternatively, a surgeon can use an anterior, lateral, and/or anterolateral approach to introduce the balloon because the balloon is introduced in a deflated state and the tools are minimal in diameter and therefore the risk of an interference with sensitive soft tissues such as nerves is reduced. A benefit is that the balloon can be inserted without removal of the facet joint of the vertebrae, as is normally required during the insertion of an intervertebral implant.

In some methods, the balloon can be rolled into a tubular shape outside the body of the patient; the shape of the balloon is selected, or the balloon is welded into its shape before it is rolled into a tubular shape. The balloon is then inserted into the body through a catheter or other tube-shaped device, and then unfurled once inside the body, or appropriate cavity, of the patient. Alternatively, the balloon can be rolled and or folded around a guide wire outside the body of the patient and then unfurled once inside the body, or appropriate cavity, of the patient. This method allows the balloon to be inserted with a low profile, in a tubular shape, and then unfurled into a flat shape because the balloon is not yet inflated. The rolled balloon can be inserted into a cavity that is pre-created or cleared, according to any of the methods described above, to encounter less resistance when it is unfurled or expanded. The balloon, or the individual compartments of the balloon, are then inflated with any of the contents necessary to restore the proper anatomy of the patient.

Referring now to the drawing, in which like reference numbers refer to like elements throughout the various figures that comprise the drawing, FIG. 1 shows a multi-volume balloon 10 with three volumes 10A, 10B, and 10C. A perforated guide tube 20 provides single channel unilateral access to the three volumes 10A, 10B, 10C of the multi-volume balloon 10. An inner tube, not shown, is inserted into the perforated guide tube 20 and contents are provided to the inner tube via a delivery tube 25. The inner tube then provides contents to volumes 10A, 10B, 10C in a method as described in connection with FIG. 3. The fixation site 27 of the delivery tube 25 secures the perforated guide tube 20 to the delivery tube 25 to create a seal and prevent contents from leaking when the multi-volume balloon 10 is inflated.

FIG. 2A is a perspective view of a connectable balloon 15 having three single volumes 15A, 15B, and 15C. The number of volumes of the connectable balloon 15 can be determined before surgery (i.e., can be "predetermined") or additional volumes can be added to the connectable balloon 15 during surgery. By "predetermined" is meant determined beforehand, so that the predetermined characteristic (number of volumes) must be determined, i.e., chosen or at least known, in advance of some event (surgery). FIG. 2A shows the connectable balloon 15 with three volumes 15A, 15B, and 15C. The volumes 15A, 15B, and 15C each contain a connectable perforated guide tube portion 23A, 23B, and 23C providing access to each of the volumes 15A, 15B, and 15C, respectively.

FIG. 2B is a perspective view of the connectable balloon 15 formed into a multi-volume balloon. The volumes 15A, 15B, and 15C are connected via the connected perforated guide tube 23. Specifically, the connectable perforated guide tube portions 23A, 23B, and 23C each contain a fixation site 28 that allows the connectable perforated guide tube portions 23A, 23B, and 23C to connect and form a multi-volume connectable balloon 15. The perforated guide tube 23 can be made of any suitable material, preferably a metal, and more preferably nickel titanium to provide a stiff, predetermined shape. The connected perforated guide tube 23 provides single channel unilateral access to the volumes 15A, 15B, and 15C. An inner tube, not shown, is inserted into the connected perforated guide tube 23. The inner tube then provides contents to volumes 15A, 15B, 15C in a method as described in connection with FIG. 3. A delivery tube provides contents to the inner tube that provides for inflation of each of the volumes 15A, 15B, and 15C. In an alternative embodiment, volumes 15A, 15B, and 15C are inflated simultaneously.

Although three volumes 15A, 15B, and 15C are shown in FIGS. 2A and 2B for the illustrated embodiment of the connectable balloon 15, the number of volumes is not limited to three. Two, four, or more volumes are suitable. The number of volumes are selected to meet the requirements of a particular patient and application. For example, the number of volumes might be determined by the width of the vertebral bodies with which the volumes must interact. Thus, the connectable balloon 15 offers a modular system. An x-ray or other imaging technique can be used to determine how many volumes are needed. The caretaker can then mount or load the requisite number of volumes outside the patient and ready those volumes for delivery. In an alternative embodiment, the volumes can be mounted inside the patient if the caretaker determines that more volumes are needed during the application of the multi-volume balloons.

Figure 3:
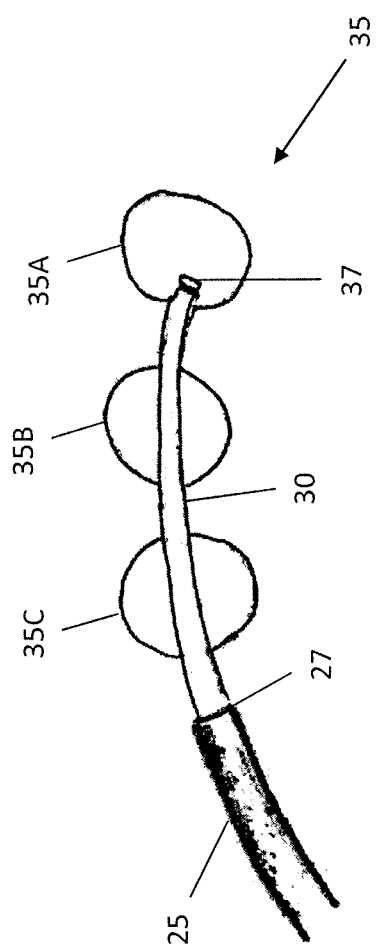
FIG. 3 is a perspective view of the structure used to inflate and adjust a multi-volume balloon according to an embodiment.

FIG. 3 is a perspective view of the structure used to perform the method of inflating and adjusting a multi-volume balloon 35. The method is also applicable to inflating and adjusting the multi-volume balloon of FIG. 1 (multi-volume balloon 10) or FIG. 2B (connectable balloon 23). FIG. 3 shows a multi-volume balloon 35 with three volumes 35A, 35B, and 35C. An inner tube 30 is inserted into a perforated guide tube, not shown, that provides single channel unilateral access to the three volumes 35A, 35B, and 35C. In another embodiment of the method, the perforated guide tube is not needed. The inner tube 30 delivers contents to inflate each of the volumes 35A, 35B, and 35C. The contents are provided to the inner tube 30 from the delivery tube 25. The fixation site 27 of the delivery tube 25 secures the perforated guide tube to the delivery tube 25 to create a seal and prevent contents from leaking when the multi-volume balloon 35 is inflated.

A problem in the art is that a posterior approach to the vertebral disc has a very limited path during surgery, especially if the tools used by the surgeon are all straight tools. The surgeon must navigate around corners and has a difficult time gaining access to the entire intervertebral disc and placing any device in the proper location. Therefore, an embodiment provides that the perforated guide tube is pre-shaped with a curve to provide easier access for the surgeon to the intervertebral disc and space. Another solution to this problem provided involves the steps of introducing the multi-volume balloon in a deflated state, with a reduced profile, and then inflating the balloon once it is delivered to the desired location. Still another solution to this problem is achieved by inserting the device in a deflated state with small diameter equipment; therefore, a surgeon can use an anterior approach to insert the balloon and avoid the limitations of the posterior approach.

The method implemented using the structure of FIG. 3 provides for a one piece-multi-volume balloon for improved load distribution that provides a flexible system for individual intra-operative length modification of the balloon. The method provides for first inflating the volume 35A most distal to the delivery tube 25. The terms "distal" or "distal end" are used to define the part or surface of an element which is facing the patient or positioned furthest from the user. The terms "proximal" or "proximal end" are used to define the part of the surface of an element which is facing away from the patient or positioned closest to the user. The inner tube 30 is used to fill each volume of the multi-volume balloon 35 one-by-one: first the distal-most volume 35A is filled, then the delivery tube 25 is retracted slightly and the next most distal volume 35B is filled, and so on until the proximal volume 35C is filled. In some embodiments, delivery tube 25 is an access tube with a working channel and fixation site 27 is the opening with an inner tube that provides content to the delivery tube 25. After filling the balloon 35, delivery tube 25 is released. The multi-volume balloon 35 is segmentally dilated with the contents as the inner tube 30 is retracted. The inner tube 30 delivers contents to volume 35A to provide for adjustment as needed. Inner tube 30 is then moved more proximal to delivery tube 25 to provide contents to volume 35B. Inner tube 30 is then moved more proximal to delivery tube 25 to provide contents to volume 35C.

The amounts of contents delivered to volumes 35A, 35B, and 35C do not need to be equal; a purpose of the balloon 35 is to form fit the volumes 35A, 35B, and 35C to the anatomy of the cavity. Each volume 35A, 35B, 35C is provided the amount of contents needed to adjust and stabilize the bone in the area of bone contacted by an individual volume. For example, volume 35A contacts an area within the cavity of the bone different from volume 35B or volume 35C. Depending upon the amount of volume needed to fill the cavity and stabilize the bone, the amount of contents in each volume 35A, 35B, and 35C can be varied. The adjustment of each volume 35A, 35B, and 35C can be done in situ so that a surgeon can determine if the bone is stabilized based on the amount of contents in each volume 35A, 35B, and 35C. This adjustment provides for a one-step filling process of the complete system. Different pressures are applied to fill the respective volumes based upon the individualized need of the patient. Once the surgeon is satisfied that the amount of contents in each volume 35A, 35B, and 35C has stabilized the bone, inner tube 30 is then removed from the perforated guide tube and the perforated guide tube remains in situ and is sealed off to prevent contents from leaking out of the multi-volume balloon 35. A marker 37 can be added to the distal end of inner tube 30. The marker 37 shows the position of the end, allowing the surgeon to locate the end during surgery. In an alternative embodiment, the marker 37 includes a heating element in order to selectively apply heat to the content material of the multi-volume balloon 35 once the balloon 35 is inserted into the patient.

In another embodiment, multi-volume balloon 35 can be inserted in the patient and each volume 35A, 35B, and 35C is filled at the same time. Each volume is filled with individual pressure and dilation control for correction of an angle of the vertebral bodies, such as, for example, correction of an angle in an anterior or posterior position or correction of scoliosis by lateral positioning.

In yet another embodiment, multi-volume balloon 35 is inserted in the patient and each volume is filled with a different filler for a different purpose. For example, volume 35A is filled with a temporary, non-rigid, filler such as saline solution for lifting and correction purposes. In this embodiment, volume 35A acts as a load bearing "cage" volume and it is preferable that volume 35A is made of stronger materials to withstand the load-bearing forces. Volumes 35B and 35C are then filled with a long-term, rigid filler such as a hydrogel or PMMA as discussed above, to act as the implant. The contents of volume 35A are then removed and the long-term filler is injected into volume 35A.

In an alternative embodiment, multi-volume balloon 35 can be inflated and shaped prior to insertion into a cavity of a patient. In this embodiment, the patient undergoes pre-surgical evaluation to determine the volume needed to fill the cavity, i.e., the space occupied by a healthy intervertebral disc, a cavity of a vertebral body, or an interspinous space. The number of volumes of multi-volume balloon 35 needed to occupy the cavity is adjusted based on a pre-surgical assessment. The number of volumes of multi-volume balloon 35 can be adjusted prior to or during surgery.

One embodiment is a kit that uses three, separate tubes: a perforated guide tube, an inner tube 30, and a delivery tube 25. The perforated guide tube remains in the body after surgery. The inner tube 30 and the delivery tube 25 are removed after the volumes 35A, 35B, and 35C of the multi-volume balloon 35 are inflated.

Figure 4:
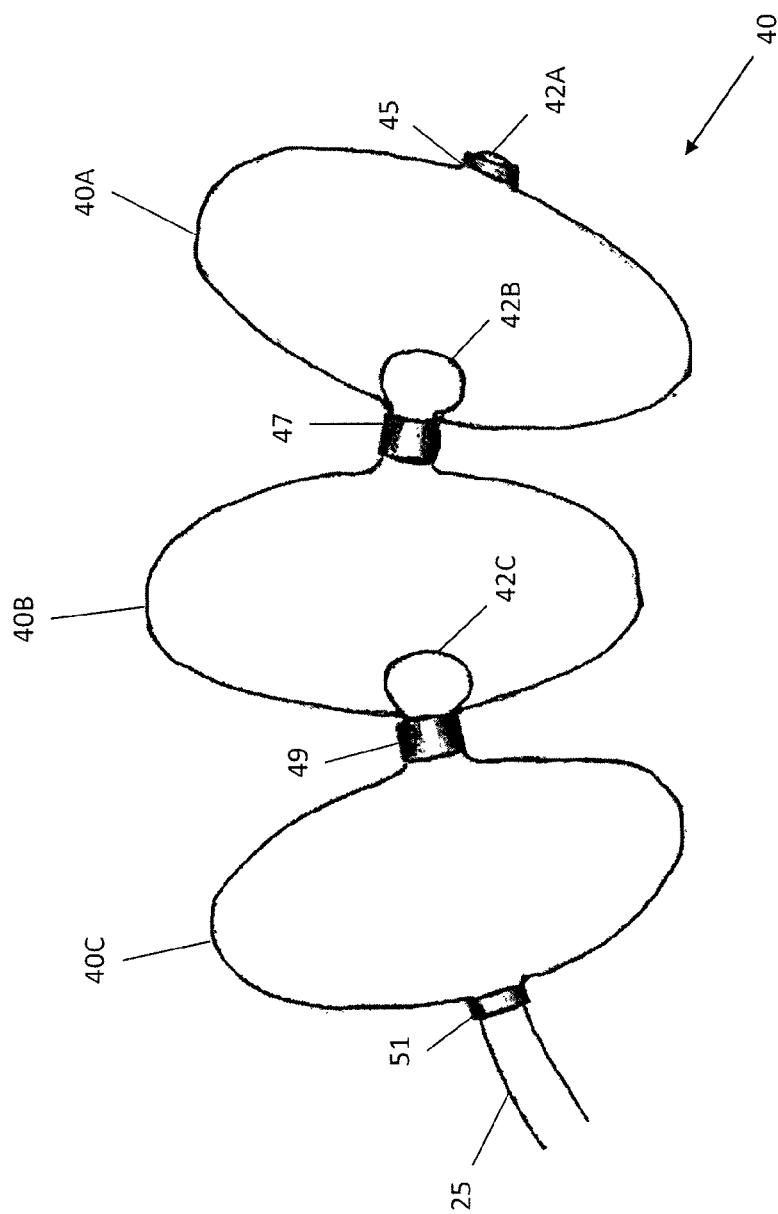
FIG. 4 is a perspective view of multiple single-volume balloons mounted in a series to form a multi-volume balloon according to an embodiment.

FIG. 4 is a perspective view of three single volumes 40A, 40B, and 40C mounted into a multi-volume balloon 40. In this aspect, volume 40A is sealed off with a ring 45 to create a seal 42A and to provide guidance for delivery tube 25. Rings are preferably made of metal to act as markers to guide the surgeon. Alternatively or in addition, the rings can act as a seal to prevent contents from leaking out of the balloons. Volume 40A is inserted into a cavity of a patient. Delivery tube 25 is connected to volume 40A and provides contents to inflate volume 40A to the desired amount. A ring 47 then seals off the contents of volume 40A to prevent leakage of the contents of volume 40A into the cavity. Ring 47 also provides guidance for insertion of volume 40B into the cavity. Volume 40A is punctured through ring 47 and volume 40B is inserted into volume 40A through ring 47. Any suitably sharp device can be used to puncture. Volume 40B is then inflated, including a portion of volume 40B that is included in volume 40A through ring 47 creating an inflated seal 42B. Seal 42B provides tension on ring 47 when inflated so the contents of volume 40B do not leak into the cavity. The volumes 40A, 40B, and 40C may be mounted in a straight line. In alternative embodiments, volumes 40A, 40B, and 40C may be mounted randomly or in a zig-zag pattern.

When volume 40B is inflated, a ring 49 then seals off the contents of volume 40B. Ring 49 also provides guidance for insertion of volume 40C into the cavity. Volume 40B is punctured through ring 49 and volume 40C is inserted into volume 40B through ring 49. Volume 40C is then inflated, including a portion of volume 40C that is included in volume 40B through ring 49 creating an inflated seal 42C. Seal 42C provides tension on ring 49 when inflated so the contents of volume 40C do not leak into the cavity. When volume 40C is inflated, a ring 51 then seals off the contents of volume 40C. Rings 45, 47, 49, and 51 provide guidance for the surgeon to insert delivery tube 25 and locate the sealed portions of volumes 40A, 40B, and 40C. Volumes 40A, 40B, and 40C are each inflatable and adjustable to different volumes to provide customized stabilization of the cavity of each patient.

Rings 45, 47, 49, and 51 are preferably thin (e.g., 0.1 to 0.4 mm wall thickness) because the entire multi-volume balloon 40 may have to be retracted and, during retraction, the rings 45, 47, 49, and 51 must not "catch" on tissues, nerves, and other objects. The rings 45, 47, 49, and 51 can be made of any suitable material. Metal is preferred for its stiffness and other qualities. Preferably, the material of the rings 45, 47, 49, and 51 can act as a marker to inform the surgeon of the precise locations of each of the rings 45, 47, 49, and 51. Suitable metals include tantalum, stainless steel, and titanium (although titanium is not as good a marker).

Rings 45, 47, 49, and 51 can comprise a one-way valve, namely, a valve that allows a liquid to flow only in one direction and not the opposite direction. U.S. Pat. No. 5,181,921 issued to Makita et al. entitled "Detachable balloon with two self-sealing valves" describes a one-way valve (the contents of this patent are fully incorporated by reference in this document). A simple membrane, or sealant of the contents, can also function as a one-way valve. The specific one-way valve can be selected, as within the skill of an artisan, to meet the needs of a particular patient and application.

In other embodiments of the invention, the puncture of volume 40A, 40B, and/or 40C does not have to be accomplished through the ring. The volume can be punctured anywhere on its surface and a one-way valve or seal will prevent the contents from leaking out of the volume.

In an alternative embodiment, the multi-volume balloon 40 can be inflated and shaped before insertion into a cavity of a patient. In this embodiment, the patient undergoes pre-surgical evaluation to determine the number of volumes needed to fill the cavity. The number of volumes of multi-volume balloon 40 can then be adjusted prior to or during surgery.

Although the invention has been described with reference to certain preferred embodiments, it should be kept in mind that the scope of the invention is not limited to these embodiments. The balloon can be modified or extended to accommodate particular formulations of balloon construction materials or fabrication techniques. Similarly, the number and spacing of the single volumes of the multi-volume balloon may be changed to better accommodate the cavity. Different balloon materials and surface coatings, or outer layers of different materials or surface coatings, may also be applied to the balloon to facilitate a smaller balloon profile for deployment. The embodiments above can also be modified so that some features of one embodiment are used with the features of another embodiment. One skilled in the art may find variations of these preferred embodiments which, nevertheless, fall within the spirit of the invention, whose scope is defined by the claims set forth below. It is also expressly intended that the steps of the methods of using the various balloons disclosed above are not restricted to any particular order.

What is claimed:

1. A multi-volume balloon for treating the clinical consequences of degenerative disc disease, vertebral body bone defects, and spinal motion segment instability comprising:
   a plurality of single volumes each connected, directly or indirectly, to one another,
   a fill tube configured to be inserted through the plurality of single volumes,
   a perforated guide tube contained within the multi-volume balloon and extending through each of the single-volumes,
   wherein each single volume is individually and independently adjustable and expandable and configured to maintain said individual and independent adjustment and expansion after the fill tube is removed therefrom, such that
   (a) each single volume can contain a variable volume of contents, and
   (b) each of the plurality of single volumes can contain the same, or a different, amount and type of contents relative to another single volume.

2. The multi-volume balloon according to claim 1, wherein
   the fill tube is adapted to be inserted into the perforated guide tube,
   wherein the fill tube is capable of delivering contents to the plurality of single volumes and the amount of contents delivered to the plurality of single volumes is adjustable and variable in each volume; and a delivery tube is attached to the fill tube, wherein the delivery tube is adapted to be connectable to the perforated guide tube.

3. The multi-volume balloon according to claim 2, wherein the single volumes are connected via the perforated guide tube to form the multi-volume balloon.

4. The multi-volume balloon according to claim 2, wherein the perforated guide tube is flexible and pre-shaped into a curved formation.

5. The multi-volume balloon according to claim 1 further comprising a ring configured to create a seal between two connected and expanded single volumes, wherein the two single volumes are connected via a puncture in a first single volume that contains a section of the second single volume and secured by the ring connecting the first and second single volumes to form the multi-volume balloon.

6. The multi-volume balloon according to claim 5 further comprising: a third single volume connected to the second single volume of the multi-volume balloon via a puncture in the second single volume of the multi-volume balloon and secured by a second ring connecting the second single volume and the third single volume to form the multi-volume balloon comprising three single volumes.

7. The multi-volume balloon according to claim 5 wherein the ring is a one-way valve.

8. The multi-volume balloon according to claim 1, wherein each of the single volumes is external to the other single volumes.

9. The multi-volume balloon according to claim 1, further comprising rigid contents.

10. The multi-volume balloon according to claim 9, wherein the rigid contents include bone cement.

11. The multi-volume balloon according to claim 1, wherein the fill tube is configured to extend through an entire length of at least one of the single volumes.

12. The multi-volume balloon according to claim 1, wherein the volume of contents in a first single volume is not limited by the volume of contents in a second single volume.

13. A kit for aligning and stabilizing a bone, the kit comprising:

a multi-volume balloon including a plurality of adjustable single-volume balloons each connected, directly or indirectly, to one another;

a perforated guide tube contained within the multi-volume balloon and extending through each of the single-volume balloons;

a fill tube adapted to be inserted into the perforated guide tube and capable of delivering contents to the plurality of single-volume balloons; and a delivery tube adapted to be connected both to the fill tube and to the perforated guide tube, wherein each single-volume balloon is individually and independently adjustable and expandable and configured to maintain said independent adjustment and expansion after the fill tube is removed therefrom, such that (a) each single-volume balloon can contain a variable volume of contents, and (b) each of the plurality of single-volume balloons can contain the same, or a different, volume of contents relative to another single-volume balloon.

14. The kit according to claim 13, wherein each of the single-volume balloons is external to the other single-volume balloons.

15. The kit according to claim 13, further comprising rigid contents.

16. The kit according to claim 15, wherein the rigid contents include bone cement.

17. The kit according to claim 13, wherein the fill tube extends through an entire length of at least one of the single-volume balloons.

18. The kit according to claim 13, wherein the volume of contents in a first single-volume balloon is not limited by the volume of contents in a second single-volume balloon.

* * * * *